(12) United States Patent
Hall et al.

(10) Patent No.: US 7,008,418 B2
(45) Date of Patent: Mar. 7, 2006

(54) MAGNETICALLY ASSISTED PULMONARY VEIN ISOLATION

(75) Inventors: Andrew F. Hall, St. Charles, MO (US); Roger N. Hastings, Maple Grove, MN (US)

(73) Assignee: Stereotaxis, Inc., St. Louis, MO (US)

( * ) Notice: Subject to any disclaimer, the term of this patent is extended or adjusted under 35 U.S.C. 154(b) by 86 days.

(21) Appl. No.: 10/435,713

(22) Filed: May 9, 2003

(65) Prior Publication Data

US 2004/0034347 A1 Feb. 19, 2004

Related U.S. Application Data

(60) Provisional application No. 60/379,204, filed on May 9, 2002.

(51) Int. Cl.
*A61B 18/18* (2006.01)

(52) U.S. Cl. .......................................... 606/41; 607/122

(58) Field of Classification Search ........ 607/126–128, 607/88–103, 115–116, 119, 101, 102, 122; 606/1–52; 600/374–375, 585
See application file for complete search history.

(56) References Cited

U.S. PATENT DOCUMENTS

| | | | |
|---|---|---|---|
| 5,842,984 A * | 12/1998 | Avitall | 600/374 |
| 6,325,797 B1 * | 12/2001 | Stewart et al. | 606/41 |
| 6,385,472 B1 * | 5/2002 | Hall et al. | 600/374 |
| 6,402,746 B1 * | 6/2002 | Whayne et al. | 606/41 |
| 6,529,756 B1 * | 3/2003 | Phan et al. | 600/374 |
| 6,645,199 B1 * | 11/2003 | Jenkins et al. | 606/41 |

* cited by examiner

*Primary Examiner*—Michael Peffley
(74) *Attorney, Agent, or Firm*—Harness Dickey & Pierce PLC (57) ABSTRACT

A method for forming an ablation pattern to electrically isolate a vessel having an ostium from a chamber formed within a patient for treatment of cardiac arrhythmia. The distal portion of a catheter is navigated to a chamber. An anchor member is deployed from the distal end of the catheter into the chamber, and the distal end is navigated into the ostium of the vessel, and temporarily secured in the vessel. An ablation member is deployed from the distal end of the catheter into the chamber and successively navigated into contact with tissue adjacent the ostium and ablating the tissue in contact with the ablation member to form a line of ablation. At least one of the navigating the distal portion of the catheter, navigating the anchor member and navigating the ablation member is performed by applying an external magnetic field to orient the device being navigated.

1 Claim, 9 Drawing Sheets

MAGNETICALLY ASSISTED PULMONARY VEIN ISOLATION

CROSS REFERENCE TO RELATED APPLICATION

This application claims priority from provisional patent application Ser. No. 60/379,204, filed May 9, 2002, the disclosure of which is incorporated herein by reference.

BACKGROUND OF THE INVENTION

This invention relates to a system for and method of isolating tissue for the treatment of cardiac arrhythmia, and in particular to a system and method of magnetically assisted pulmonary vein isolation.

The heart includes a number of pathways that are responsible for the propagation of signals necessary to produce continuous, synchronized contractions. Each contraction cycle begins in the right atrium where a sinoatrial node initiates an electrical impulse. This electrical impulse then spreads across the right atrium to the left atrium, stimulating the atria to contract. The impulse continues from the atria to the ventricles by passing through the atrioventricular (AV) node or junction, which acts as an electrical gateway to the ventricles. The AV junction delays the signal to the ventricles, so the atria can relax before the ventricles contract.

Disturbances in the heart's electrical system may lead to various rhythmic problems that can cause the heart to beat irregularly. Irregular heart beats, or arrhythmia, are caused by physiological or pathological disturbances in the discharge of electrical impulses from the sinoatrial node, in the transmission of the signal through the heart tissue, or spontaneous, unexpected electrical signals generated within the heart. One type of arrhythmia is tachycardia, which is an abnormal rapidity of heart action. There are several different forms of atrial tachycardia, including atrial fibrillation and atrial flutter. With atrial fibrillation, instead of a single beat, numerous electrical impulses are generated by depolarizing tissue at one or more locations in the atria (or possibly other locations). These unexpected electrical impulses produce irregular, often rapid heartbeats in the atrial muscles and ventricles. Patients experiencing atrial fibrillation may suffer from fatigue, dizziness and even stroke. In fact, atrial fibrillation can increase the risk of stroke by up to five times.

The cause of atrial fibrillation, and in particular the depolarizing tissue causing "extra" electrical signals, is currently under investigation. The undesired electrical impulses often originate in the left atrial region of the heart. Studies suggest that nearly 90% of these "focal triggers" or electrical impulses are generated within and around one (or more) of the four pulmonary veins (PV) which enter from the left atrium. In this regard, as the heart develops from an embryonic stages, left atrial conductive muscle tissue my grow or extend a short distance into one or more of the PVs. It has been postulated that this tissue may spontaneously depolarize, resulting in an unexpected electrical impulse(s) propagating in to the left atrium, and long the various electrical pathways of the heart.

A variety of different atrial fibrillation treatment techniques are available, including drugs, surgery, implants, and catheter ablation. Drugs typically only mask the symptoms and do not cure the underlying cause. Implantable devices usually correct an arrhythmia only after it occurs (and are better suited for bradycardia than tachycardia). Surgical and catheter-based treatments, in contrast, will have the potential to actually cure the problem by ablating the abnormal tissue or accessory pathway responsible for the atrial fibrillation. Catheter-based treatments rely on the application of various destructive energy sources to the target tissue, including electrical energy, radio frequency electrical energy, laser energy, cryocooling, and the like. The energy source, such as an ablating RF electrode, is normally disposed along a distal portion of a catheter.

Most ablation catheter techniques employed to treat atrial fibrillation focus on locating the ablating electrode, or a series of ablating electrodes, along extended target sections of the left atrial wall. Because the atrium wall, and thus the targeted site(s), is relatively tortuous, the resulting catheter design includes multiple curves, bends, extensions, etc. In response to recent studies indicating that the unexpected electrical impulses are generated within a PV, efforts have been made to ablate tissue within the PV itself. However, ablation of tissue in the PV itself may cause the PV to shrink or constrict. Because PV's have a relatively small diameter, a stenosis may result. An occluded PV results in the loss of up to one quarter of the lungs function as there is no redundant blood path. Even further, other vital bodily structures are directly adjacent each PV. These structures may be undesirably damaged when ablating within a PV, such as the frenic nerve which controls the diaphragm.

As a result, it is desirable to form a continuous ablation lesion pattern in the left atrium wall about the ostium of the particular PV, to electrically isolate the PV from the left atrium. As a result, any undesired electrical impulse generated within the PV could not propagate into the left atrium, thereby eliminating unexpected atria contraction. However, while PV isolation via a continuous ablation lesion pattern about the PV ostium appears highly viable, it can be difficult to achieve. It is difficult to form the necessary continuous line of ablation with conventional EP catheters. Some devices have been developed to facilitate PV isolation, including those disclosed in U.S. Pat. No. 6,325,797, for Ablation Catheter And Method For Isolating A Pulmonary Vein; U.S. Pat. No. 6,314,963, for Method Of Ablating Tissue From An Epicardial Location; U.S. Pat. No. 6,314,962, for Method Of Ablating Tissue Around The Pulmonary Veins; U.S. Pat. No. 6,311,692, for Apparatus And Method For Diagnosis And Therapy Of Electrophysiological Disease; and U.S. Pat. No. 6,237,605, for Methods Of Epicardial Ablation; U.S. Pat. No. 6,161,543, for Methods Of Epicardial Ablation For Creating A Lesion Around The Pulmonary Veins, the disclosures of which are incorporated herein by reference, but it is still difficult to perform a PV isolation procedure.

A related concern entails mapping of a PV prior to ablation. In cases of atrial fibrillation, it is desirable to identify the origination point of the undesired electrical impulses prior to ablation. Thus, it must first be determined if the electrical impulse originates within one or more PVs. However the foci that cause atrial fibrillation do not always fire when the patient is on the table, in spite of drugs and other maneuvers to induce them. One way to address this is focus-based ablation, where no ablation is made unless firing is observed in a particular part of a PV. A second way of addressing this is functional isolation. It turns out than there are directional conductive muscle fibers that enter the left atrium. These are unevenly distributed about the ostium of a given pulmonary vein such that, as one traverses the circumference of the PV, some sites will conduct and some will not. In functional isolation, only those sections of the PV circumference that conduct are ablated (although the determination of these sections is imprecise). A third way to address this is to do complete anatomical isolation of the PV;

making an ablation circle all the way around rather than only ablate active pathways into a PV.

Thus two of the method require identification of the depolarizing tissue. Once the depolarizing tissue has been identified, necessary ablation steps can be taken. Mapping is normally accomplished by placing one or more mapping electrodes into contact with the tissue in question. In order to map tissue within a PV, therefore, a relatively straight catheter section maintaining two or more mapping electrodes must be extended axially within the PV. Ablation catheters configured to slide along the atrial wall cannot include a separate, distal extension for placement within the PV. Instead, an entirely separate mapping catheter must be provided and then removed for subsequent replacement with the ablation catheter. Obviously, these additional steps greatly increase the overall time required to complete the procedure.

Electrical isolation of a pulmonary vein via an ablation lesion pattern surrounding the pulmonary vein ostium presents a potentially revolutionary technique for treatment of atrial fibrillation. However, the unique anatomical characteristics of a pulmonary vein and left atrium render currently available ablation catheters minimally useful. Therefore, a substantial need exists for an ablation catheter designed for consistent positioning of one or more ablation electrodes about a pulmonary vein ostium, as well as for providing pulmonary vein mapping information.

Currently there are two techniques in clinical use for PV isolation. These are "Lasso catheter" based and "Circumferential ablation balloon" based.

In the first method, two punctures are made in the septal wall, through which two catheters are introduced into the left atrium from the right atrium. The first is an standard ablation catheter. The second is a circular mapping catheter (e.g., a Lasso catheter). The circular catheter has a small loop at the tip with a number of electrodes on the loop. The Lasso catheter is first navigated to a pulmonary vein and positioned within the ostium. The ablation catheter is then navigated to sites near the loop part of the mapping catheter (often guided by the signals emanating from various electrodes in the loop catheter). The lasso catheter provides both electrical and anatomic targeting information for the ablation catheter. Using this information, a number of ablations are made, until the physician is satisfied that the PV is indeed isolated. The procedure may then be repeated for one or more of the other pulmonary veins. This procedure requires a double trans-septal puncture. It is often hard to know exactly where the lasso catheter has been positioned, relative to the ostium of the pulmonary veins.

This procedure requires a double transeptal puncture is required. Many physicians are untrained and/or uncomfortable with this technique, and it adds time to the procedure. More specifically, the navigation is time consuming navigation (must go from the trans-septal puncture to a particular site on a Lasso catheter multiple times). There can also be difficulties in getting the catheter to the desired location. Lesions made within the PV can contribute to PV stenosis or phrenic nerve damage. It is hard to position the catheter just outside the ostium. Foci often do not present themselves during the case, and as many as 50% of PV AF foci reside at or outside the PV's, and are not treated by blocking the signal more distal (i.e., within the PV). Each of these problems is addressed by various embodiments of this invention.

In the second technique, a single puncture is made in the atrial septal wall and a specialized catheter is advanced into the left atrium from the right atrium. (could ref Atrionix and Daig devices) The device is navigated to a pulmonary vein. A balloon at the tip of the catheter is expanded with saline and the expanding balloon anchors the device within the PV. A transducer (e.g. ultrasound) is then used to transmit energy circumferentially through the saline in the balloon, to completely isolate a PV in a single application of energy. The potential advantages are complete anatomic isolation and the quickness of the procedure.

Possible problems with this technique include the fact that PV's can be non-circular with highly variable transitions from the vein to the ostium to the chamber, and a circular balloon is not always a good fit with the anatomy, or cannot be positioned perpendicular to the ostium, which can result is in ineffective lesions. The technique often ablates within the pulmonary veins, with the risk of PV stenosis. The technique requires a transeptal puncture. The technique can miss foci that are at or just outside the ostium. Also, with this technique, these devices must be navigated manually, at the bedside with radiation and lead burden. Each of these problems is addressed by various embodiments of this invention.

SUMMARY OF THE INVENTION

The present invention is a system for, and method of, magnetically assisted ablation. The system comprises a catheter having a distal end, and anchor member telescopingly mounted in a lumen in the catheter, and an ablation member telescopingly mounted in a lumen in the catheter. There is a magnetic member associated with at least one of the distal end of the catheter, the distal end of the anchor member, or the distal end of the ablation member. The magnetic member is sized and positioned so that when a magnetic field of at least 0.1 Tesla, and more preferably of at least 0.05 Tesla causes the magnetic member and thus the structure it is attached to, to align with the applied field.

According to the method of this invention, the distal end of the catheter is navigated to the procedure site, for example the left atrium of the heart. This navigation may be by conventional mechanical mean such as internal steering wires, or it may be magnetically assisted using an applied magnetic field to orient the distal end of the catheter while the catheter is mechanically advanced, or the navigation may be entirely magnetic in which case the distal end of the catheter is oriented with an applied magnetic field, and a magnetic gradient to magnetically advance the catheter. Once the distal end of the catheter is at the procedure site, it is anchored by deploying the anchor member. The anchor member is navigated into a vessel, for example one of the pulmonary veins. This navigation may be by conventional mechanical mean such as internal steering wires, or it may be magnetically assisted using an applied magnetic field to orient the distal end of the anchor member while the anchor member is mechanically advanced, or the navigation may be entirely magnetic in which case the distal end of the anchor member is oriented with an applied magnetic field, and a magnetic gradient is applied to magnetically advance the anchor member. Once the anchor member is in the blood vessel, it is secured, for example by inflating a balloon, expanding a mechanical anchor, or the like. The ablation member is then deployed from the distal end of the catheter, and navigated to form a continuous or substantially continuous line of ablation surrounding the vessel's ostia. This navigation may be by conventional mechanical mean such as guide wires, or it may be magnetically assisted using an applied magnetic field to orient the distal end of the ablation member while the catheter is mechanically advanced, or the navigation may be entirely magnetic in which case the distal end of the catheter is oriented with an applied magnetic field, and a magnetic gradient to magnetically advance the ablation member. The ablation member may have electrodes for RF ablation, or other suitable tissue destroying means.

Thus, the catheter can be quickly and easily navigated to the procedure site, anchored in place, and a continuous or substantially continuous line of ablation made to electrically isolate the blood vessel, and block errant signals causing the arrythmia. Magnetically assisted navigation or magnetic navigation facilitate the fast and accurate control of the devices in body.

BRIEF DESCRIPTION OF THE DRAWINGS

Corresponding reference numerals indicate corresponding parts throughout the several views of the drawings.

DETAILED DESCRIPTION OF THE PREFERRED EMBODIMENT

Figure 1A:
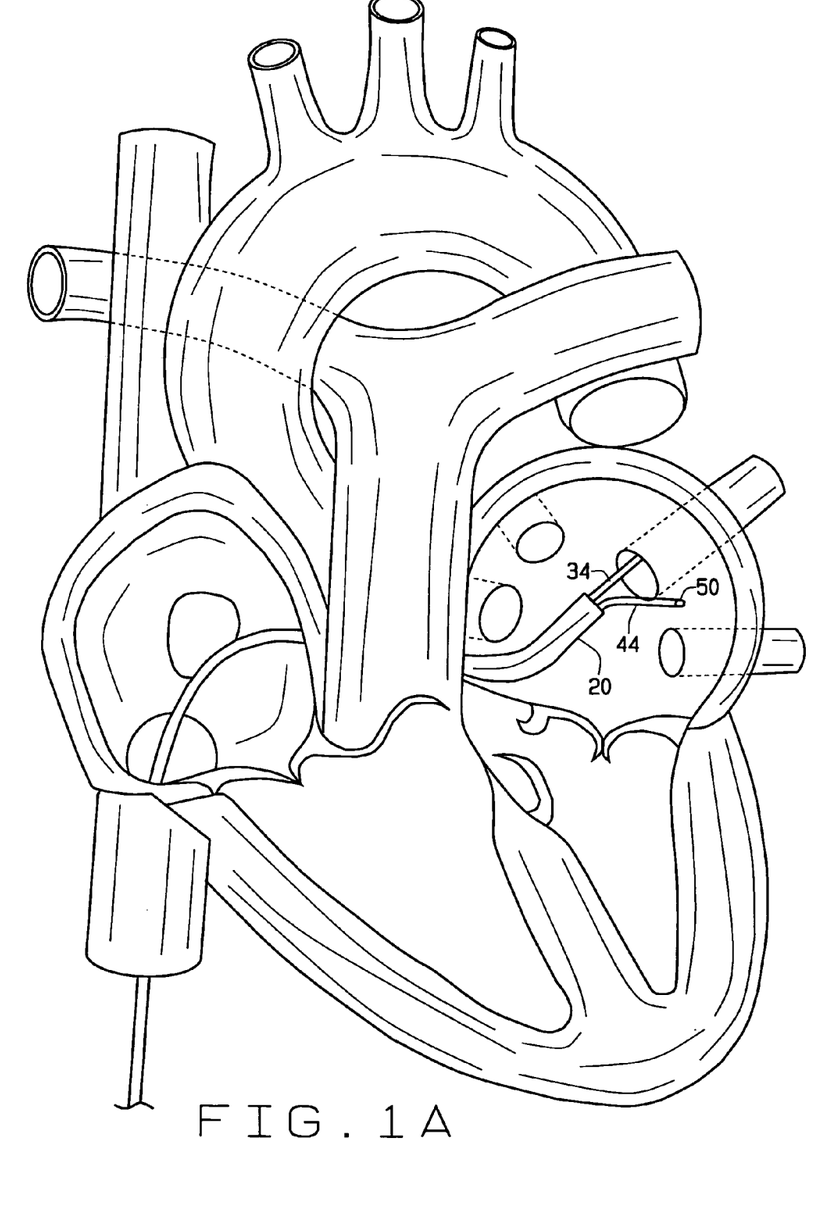
FIG. 1A is a perspective view of a heart illustrating a first embodiment of the system and method of isolating tissue, such as a pulmonary vein using a transseptal approach.
Figure 1B:
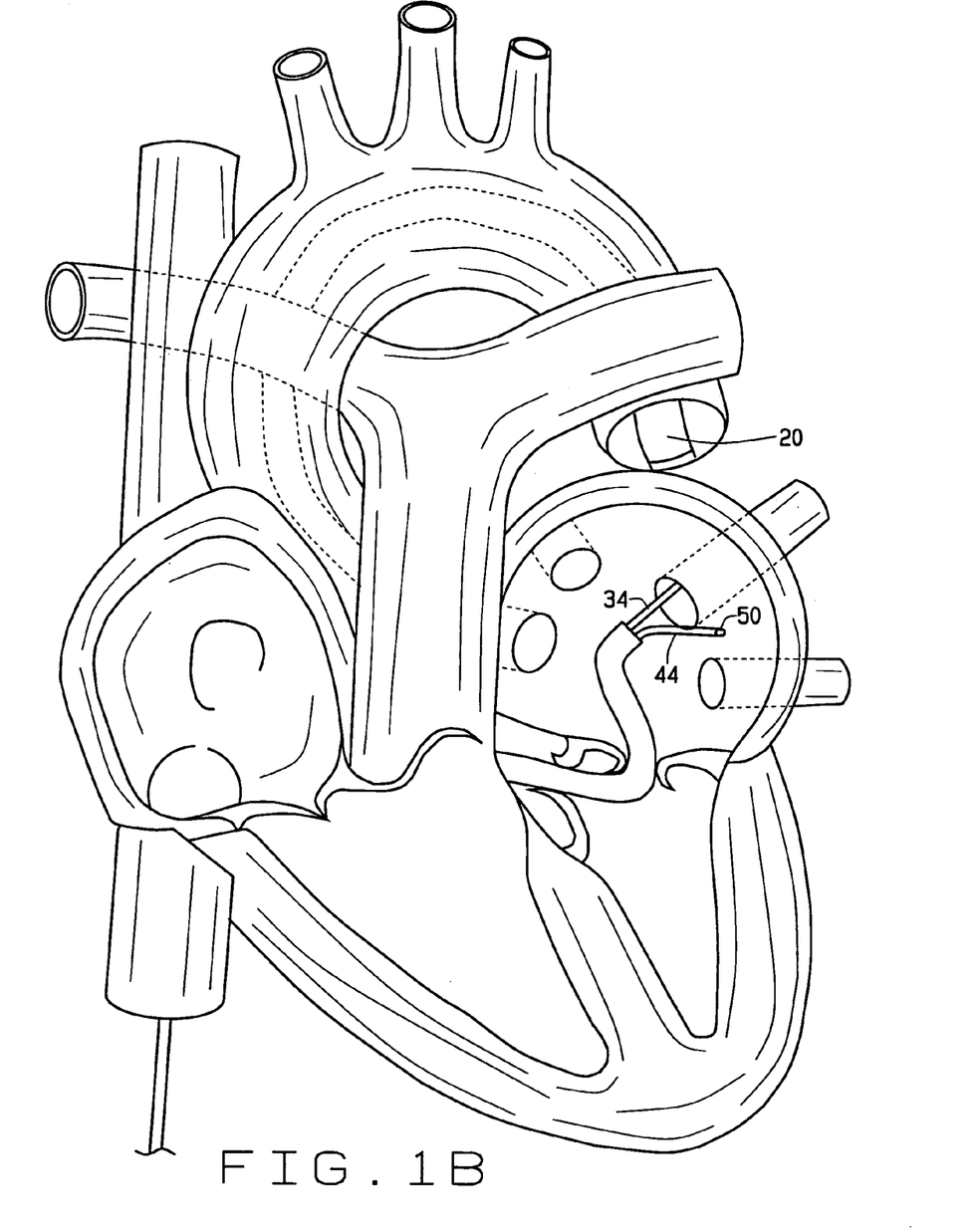
FIG. 1B is a perspective view of a heart illustrating a first embodiment of the system and method of isolating tissue, such as a pulmonary vein using a retrograde, or aortic retrograde approach.
Figure 2:
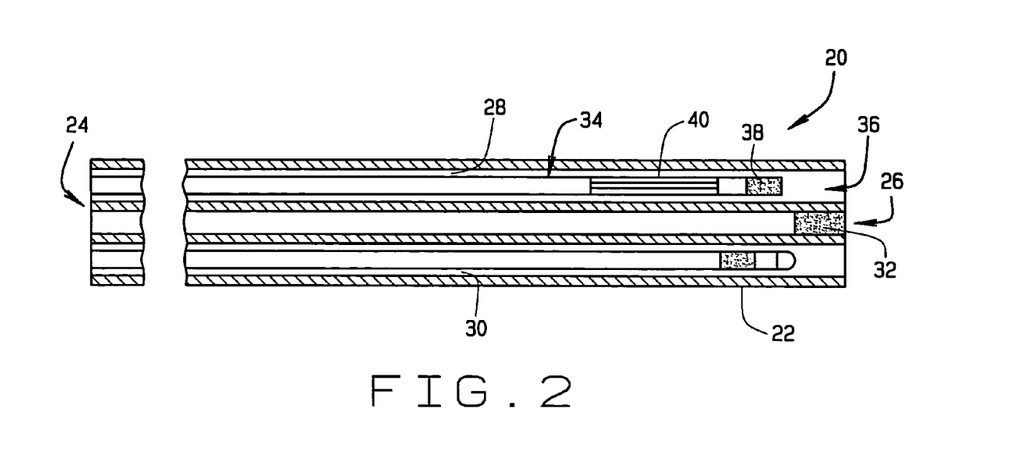
FIG. 2 is a longitudinal cross-sectional view of a first embodiment of a system constructed according to the principles of this invention.
Figure 3:
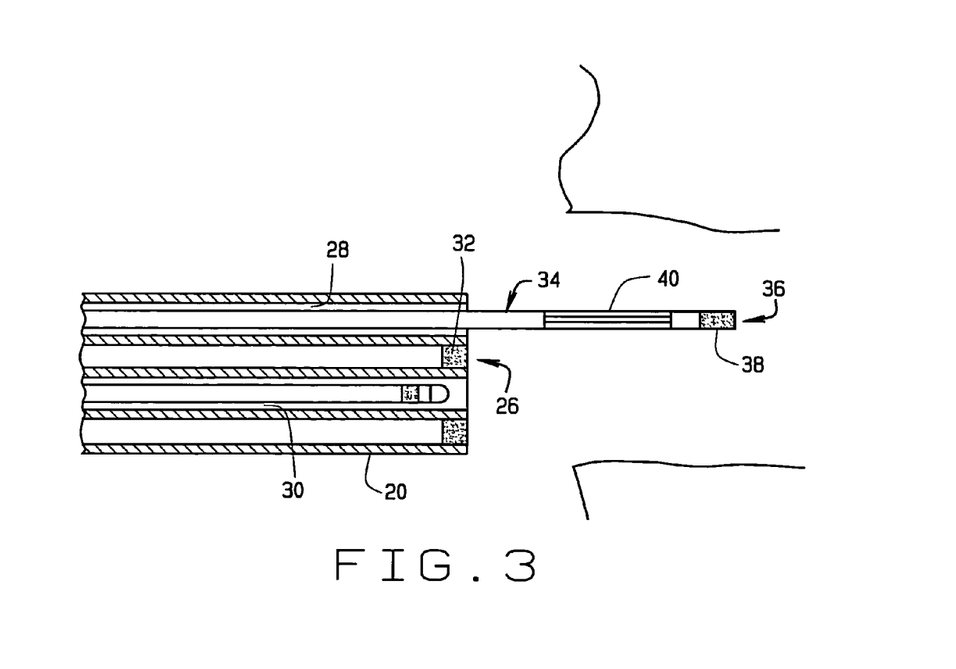
FIG. 3 is a cross-sectional view of a pulmonary vein, showing an anchor member disposed therein.

A first embodiment of a system for ablative tissue isolation constructed according to the principles of this invention is indicated generally as 20 in FIG. 2. As shown and described in this preferred embodiment, the system 20 is adapted for pulmonary vein isolation, although this invention is not limited to that procedure. As illustrated in FIG. 1 the approach can be transseptally, or as illustrated in FIG. 1A the approach can be retrograde/aortic retrograde.

The system 20 comprises a catheter 22 having a proximal end 24 and a distal end 26. At least one lumen extends through the catheter. In this preferred embodiment there are preferably two lumens 28 and 30. A magnetic member 32 is preferably disposed at or adjacent to the distal end 26 of the catheter 22. The magnetic member 32 can be a permanent magnetic material, such as Neodymium-Iron-Boron, or a permeable magnetic material such as HIPERCO. The magnetic member preferably allows the distal end 26 of the catheter 22 to be oriented with a magnetic field applied from outside the patient's body. Instead of a separate magnetic member 32 in the distal end of the catheter 22, or in addition to the magnetic member 32, one or both of an anchor member and an ablation member can be provided with a magnet member on its distal end, so that when the anchor member and the ablation member are inside the catheter, their magnetic elements can be used to orient the distal end of the catheter 22 with an applied magnetic field.

Figure 4A:
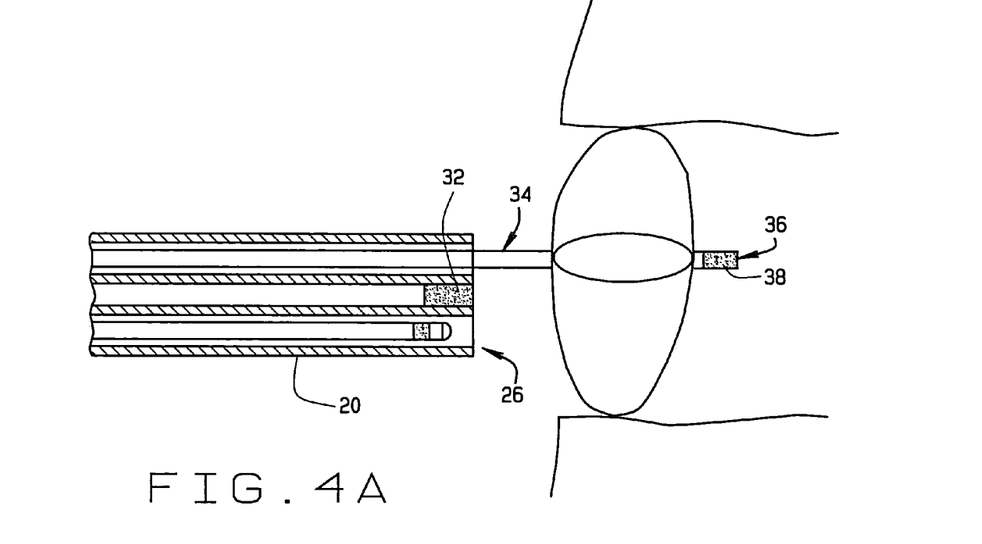
FIG. 4A is a cross-sectional view of the pulmonary vein, showing the anchor member secured in therein.
Figure 4B:
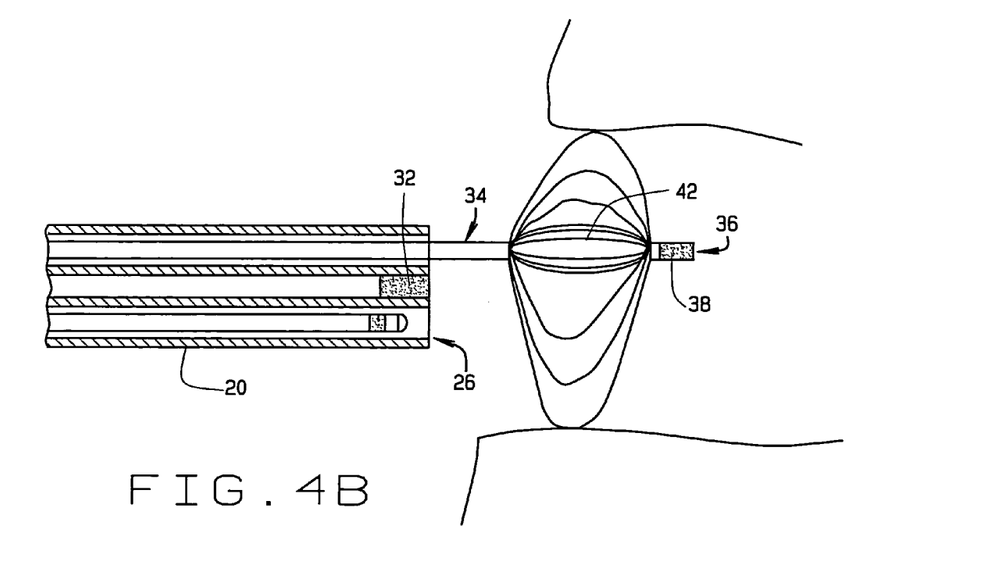
FIG. 4B is a cross-sectional view of the pulmonary vein, showing the anchor member secured in therein.
Figure 5:
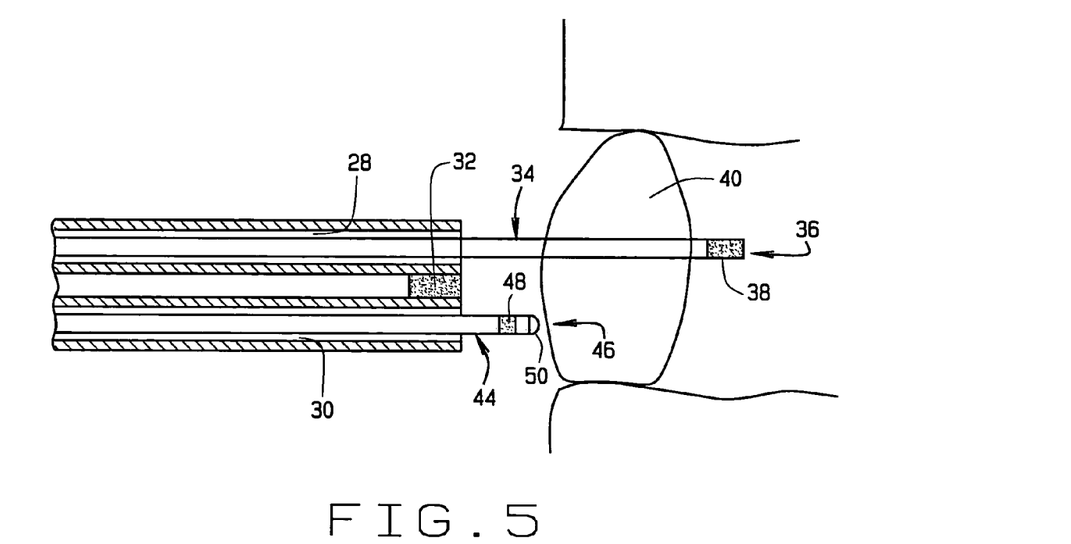
FIG. 5 is a cross sectional view of the pulmonary vein, showing the ablation member deployed.

The system 20 further comprises an anchor member 34. The anchor member 34 is preferably an elongate device having a distal end 36 telescopingly mounted in the lumen 28 in the distal end 26 of the catheter 22. The anchor member 34 is adapted to be deployed from the distal end of the catheter 22, and navigated into a site where it can be secured to secure the distal end of the catheter 22. Thus, the anchor member 34 preferably has a magnetic element 38 on its distal end 36 so that the distal end can be oriented in a desired direction with an applied magnetic field from outside the body, and mechanically advanced to the desired location, for example into one of the patient's pulmonary veins. The magnetic member 38 can be a permanent magnetic material, such as Neodymium-Iron-Boron, or a permeable magnetic material such as HIPERCO. The anchor member 34 preferably also includes a attachment member, such as an inflatable balloon 40 (FIGS. 2, 3, 4A, 5, and 6) or an expandable cage 42 (FIG. 4B) to help secure the anchor member. For example, as shown in FIG. 4A, once the anchor member 34 is in the desired pulmonary vein, the balloon 40 is inflated to engage the walls of the pulmonary vein. The balloon 40 can be provided with cutouts to permit the flow of blood past the anchor member. Alternatively, as shown in FIG. 4B, once the anchor member 34 is in the desired pulmonary vein, an expandable cage 42 can be opened to temporarily secure the anchor member in the vein. Blood can continue to flow through the openings in the cage.

The system 20 further comprises an ablation member 44 telescopingly disposed in the lumen 30. The ablation member 44 is preferably an elongate device having a distal end 46 telescopingly mounted in the lumen 30 in the distal end 26 of the catheter 22. The ablation member 44 is adapted to be deployed from the distal end of the catheter 22, and navigated to a point adjacent the ostium of the vessel in which the anchor member 34 is disposed to ablate a section of tissue surrounding the ostium. The ablation member 44 preferably has a magnetic element 48 on its distal end 46 so that the distal end can be oriented in a desired direction with an applied magnetic field from outside the body, and mechanically advanced to the desired location adjacent the ostium of the patient's pulmonary vein. The magnetic element 48 can be a permanent magnetic material, such as Neodymium-Iron-Boron, or a permeable magnetic material such as HIPERCO. There is at least one ablation electrode 50 on the distal end 46 of the ablation member 44.

Once the distal end 26 of the catheter 22 is anchored, the ablation member 44 can be deployed from the distal end of the catheter 22. The ablation member 44 preferably has a magnetic element 48 on its distal end 46 so that the distal end can be oriented in a desired direction with an applied magnetic field from outside the body, and mechanically advanced to the desired location, for example in a circular pattern around the pulmonary vein in which the anchor member 36 is secured. The distal end 46 of the ablation member 44 can have an ablation electrode 42, through which RF energy can be applied to ablate the tissue in contact with the electrode. Alternatively, the ablation member 38 can be provided with some other means for tissue ablation, including but not limited to ultrasonic ablation; cryoablation, laser ablation, etc.

Figure 6:
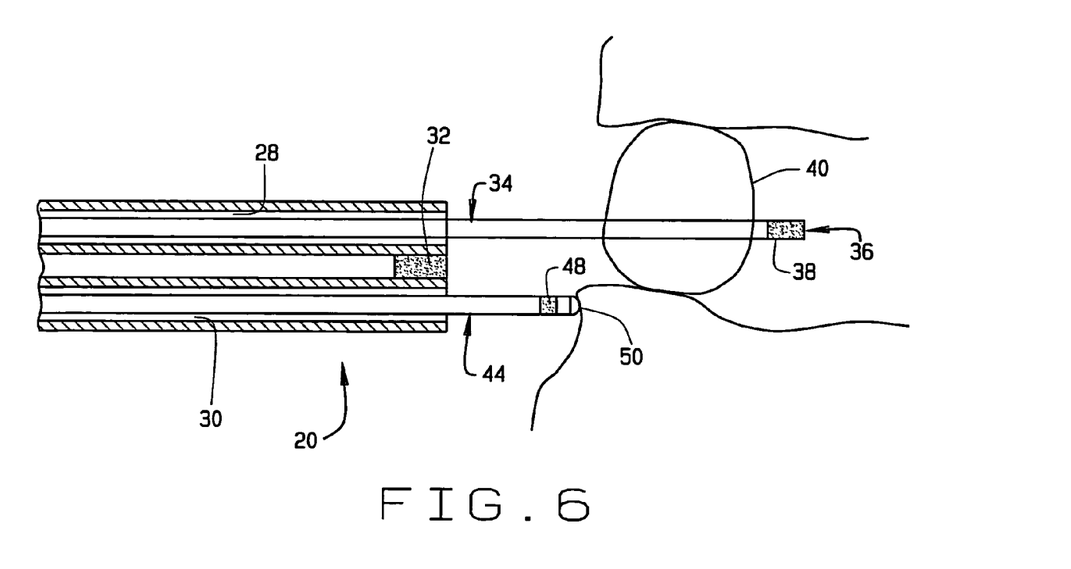
FIG. 6 is a cross-sectional view of the pulmonary vein, showing the ablation member being magnetically navigated to form a continuous line of ablation around the pulmonary vein.

The ability to magnetically control the orientation of the ablation member 44 by simply changing the direction of the externally applied magnetic field allows the member to be quickly and easily oriented to make a continuous line of ablation around the ostia of the pulmonary vein or other vessel. The advancement can even be automated with computer control advancing the ablation member to form a closed loop of ablation.

The first embodiment can also be used to in mapping instead of the ablation step, prior to the ablation step (to help determine the locations for ablation) or subsequent to the ablation step (to help determine the effectiveness of ablation). Once the distal end 26 of the catheter 22 is anchored, the a mapping member similar to ablation member 44 can be deployed from the distal end of the catheter 22. The mapping member, like ablation member 44 preferably has a magnetic element 48 on its distal end 46 so that the distal end can be oriented in a desired direction with an applied magnetic field from outside the body, and mechanically advanced to the desired location, for example in a circular pattern around the pulmonary vein in which the anchor member 36 is secured. The distal end 46 of the mapping member can have at least one mapping electrode, similar to the ablation electrode 42 on the ablation catheter 44, through which electrical activity of the tissue in contact with the electrode can be measured. Alternatively, the mapping catheter can be provided with some other sensing device for measure a physiological property of the tissue, such as temperature, can be measured. The ability to magnetically control the orientation of the mapping member by simply changing the direction of the externally applied magnetic field allows the member to be quickly and easily oriented to make a continuous line of ablation around the ostia of the pulmonary vein or other vessel. The advancement can even be automated with computer control advancing the ablation member to form a closed loop of ablation. Of course the same element can be used for both mapping and ablation, allowing the pre-ablation mapping, the ablation, and post-ablation mapping to occur continuously.

Figure 7:
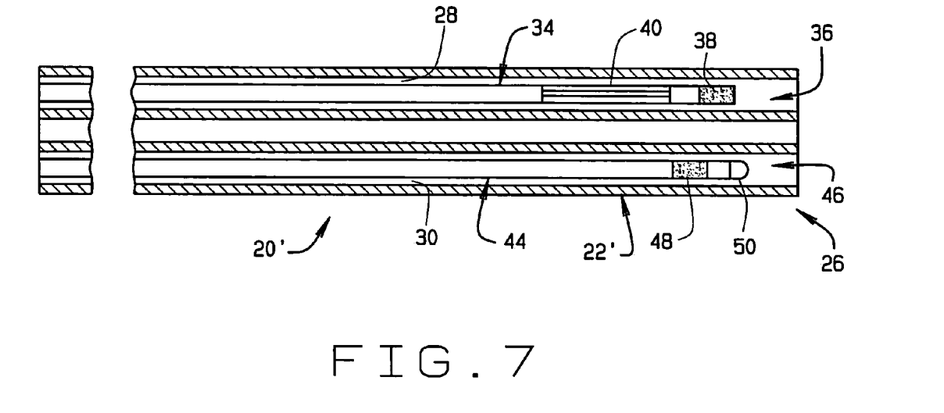
FIG. 7 is a cross-sectional view of the a second embodiment of a system constructed according to the principles of the present invention.

A second embodiment of a system constructed according to the principles of this invention is indicated generally as 20' in FIG. 7. System 20' is similar to system 20, described above, and corresponding parts are identified with corresponding reference numerals. However unlike system 20, system 20' lacks the magnetic member 32 in the distal end. Instead, the magnetic control of the distal end 26 of the catheter 20 comes from magnet member 38 on anchor member 34 and magnet member 48 on anchor member 44.

In the second embodiment of the system and method of this invention, there is a magnetic element on the distal end portion of the anchor member and the distal end portion of the ablation member. When the anchor member and the ablation member are in the catheter, their magnetic elements make the distal end of the catheter magnetically responsive to align in an applied magnetic field to facilitate navigating the distal end of the catheter to the atrium. When the distal end of the catheter is in the atrium, the anchor member is deployed from the distal end of the catheter and magnetically navigated into the pulmonary vein, and temporarily secured therein. The ablation member is then deployed into the chamber and magnetically navigated to form a continuous line of ablation around the ostium of the pulmonary vein.

Figure 8:
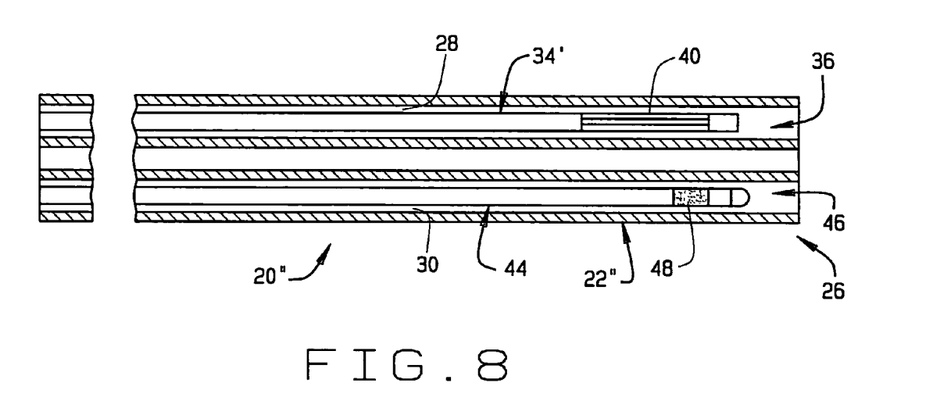
FIG. 8 is a cross-sectional view of the a third embodiment of a system constructed according to the principles of the present invention.

A third embodiment of a system constructed according to the principles of this invention is indicated generally as 20" in FIG. 8. System 20" is similar to systems 20 and 20', described above, and corresponding parts are identified with corresponding reference numerals. Like system 20', system 20" lacks the magnetic member 32 in the distal end of the catheter 20 in system 20. However, the anchor member 34" in system 20" lacks the magnetic member 38 that is present in anchor member 34 in systems 20 and 20'. Instead, the magnetic control of the distal end 26 of the catheter 20 comes from magnet member 48 on anchor member 44.

In the third embodiment of the system and method of this invention, there is a magnetic element on the distal end portion of the ablation member. When the anchor member and the ablation member are in the catheter, the magnetic element of the ablation member makes the distal end of the catheter magnetically responsive to align in an applied magnetic field to facilitate navigating the distal end of the catheter to the atrium. When the distal end of the catheter is in the atrium, the anchor member is deployed from the distal end of the catheter. The distal end of the anchor member can be independently manipulated, or it can be magnetically manipulated by moving the catheter, which is still magnetically responsive because of the undeployed ablation member. Once the distal end of the anchor member is in the pulmonary vein, it is temporarily secured therein. The catheter can be with drawn, and the ablation member deployed into the chamber. The ablation member is then deployed into the chamber and magnetically navigated to form a continuous line of ablation around the ostium of the pulmonary vein.

Figure 9:
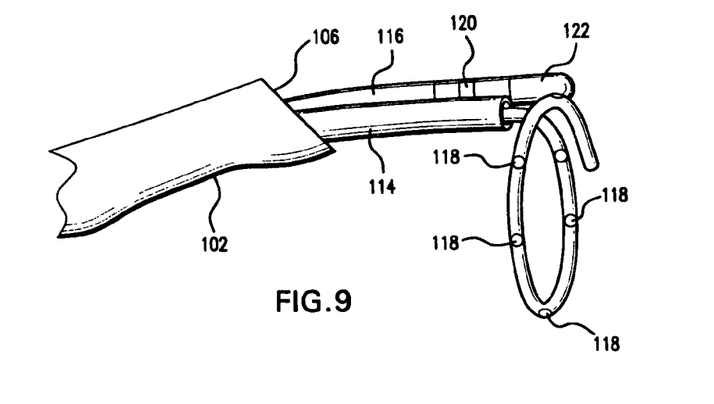
FIG. 9 is a side elevation view of the distal end of a fourth embodiment of a system constructed according to the principles of the present invention.
Figure 10:
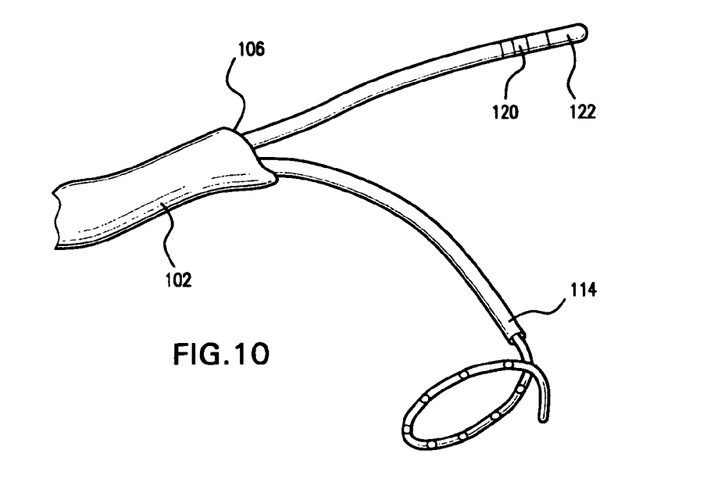
FIG. 10 is a side elevation view of the distal end of the fourth embodiment.
Figure 11:
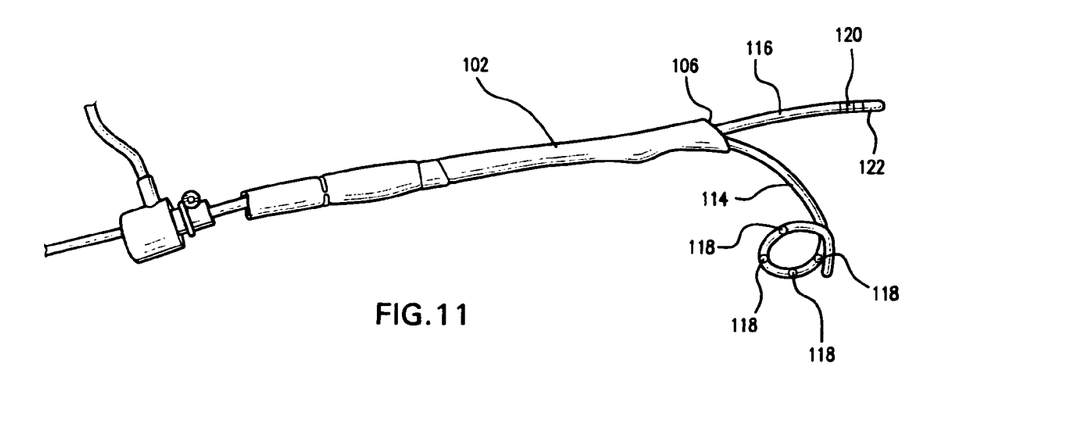
FIG. 11 is a side elevation view of the fourth embodiment

A fourth embodiment of a system constructed according to the principles of this invention is indicated generally as 100 in FIGS. 9–13. As shown in FIGS. 9–11, the system 100 comprises a catheter 102 having a proximal end and a distal end 106. At least one lumen extends through the catheter. In this preferred embodiment there are preferably two lumens. A magnetic member is preferably disposed at or adjacent to the distal end 106 of the catheter 102. The magnetic member can be a permanent magnetic material, such as Neodymium-Iron-Boron, or a permeable magnetic material such as HIPERCO. The magnetic member preferably allows the distal end 106 of the catheter 102 to be oriented with a magnetic field applied from outside the patient's body. Instead of a separate magnetic member in the distal end of the catheter 102, or in addition to the magnetic member, one or both of an anchor member 114 and an ablation member 116 can be provided with a magnet member on its distal end, so that when the anchor member and the ablation member are inside the catheter, their magnetic elements can be used to orient the distal end of the catheter 102 with an applied magnetic field.

As shown in FIGS. 9–11, the anchor member 114 is a circumferential mapping catheter, having a resilient generally circular configuration with a plurality of mapping electrodes 118 disposed thereon. The anchor member 114 can be retracted into the catheter 102, and when extended resiliently assumes a generally circular configuration that resiliently engages the interior of a pulmonary vein, such as the right inferior pulmonary vein as shown in FIG. 9.

Figure 12A:
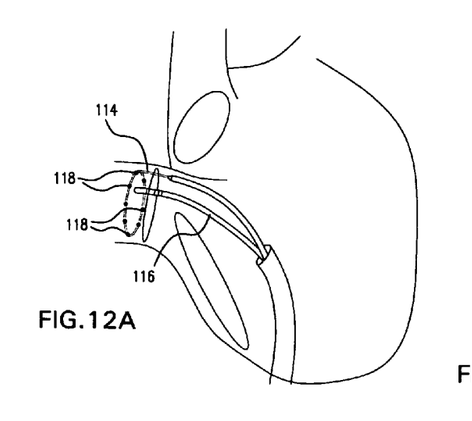
FIG. 12A is an lao xray image of a CT-based heart model, with the pulmonary veins marked, showing the circumferential mapping catheter in the right inferior pulmonary vein and anchoring the device the ablation catheter contact a point on the ostium of the right inferior pulmonary vein.
Figure 12B:
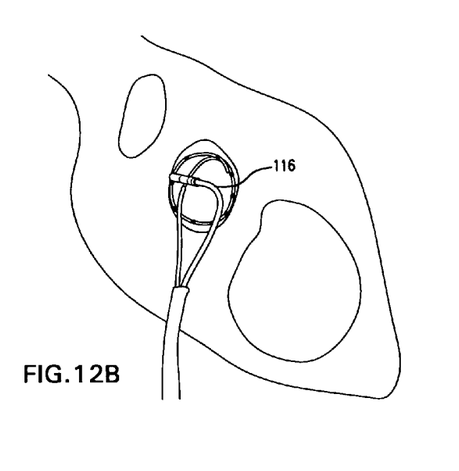
FIG. 12B is an rao xray image of FIG. 12A.
Figure 13A:
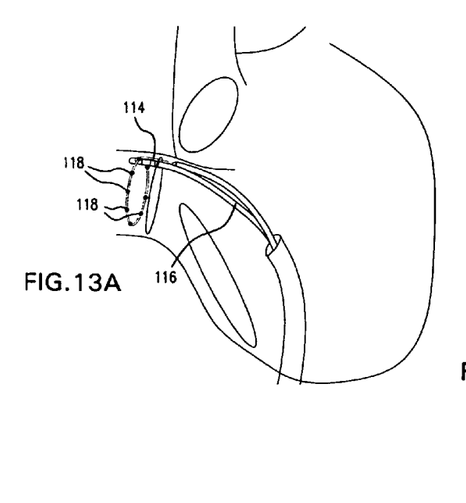
FIG. 13A is an lao xray image of a CT-based heart model, with the pulmonary veins marked, showing the circumferential mapping catheter in the right inferior pulmonary vein and anchoring the device the ablation catheter contacting another point on the circumferential mapping catheter different point on the ostium of the right inferior pulmonary vein.
Figure 13B:
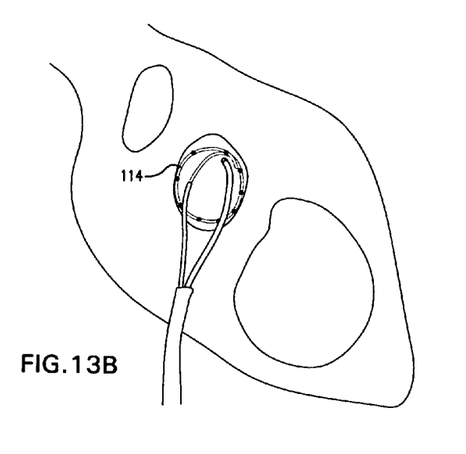
FIG. 13B is an rao xray image of FIG. 13A

Also as shown in FIGS. 9–11, the ablation member 116 has first and second electrodes 120 and 122. The ablation member 116 can be magnetically navigated around the ostium of the PV in which the anchor member 114 is disposed. Thus, as shown in FIGS. 12A and 12B, the anchor member 114 is introduced into the opening of the right inferior pulmonary vein. Due to its loop configuration, the distal end of the anchor member resiliently engages the right inferior pulmonary vein. The plurality of electrodes 118 can sense electrical activity at a plurality of locations around the circumference of the ostium of the pulmonary vein. Based upon where electrical activity is detected, the ablation member 116 can be navigated to those points, and ablate the tissue in the vicinity where electrodes 118 sensed electrical activity. FIGS. 13A and 13B show the ablation member 116 navigated to another point on the ostium wherein the anchor member 114 sensed electrical activity.

Figure 14A:
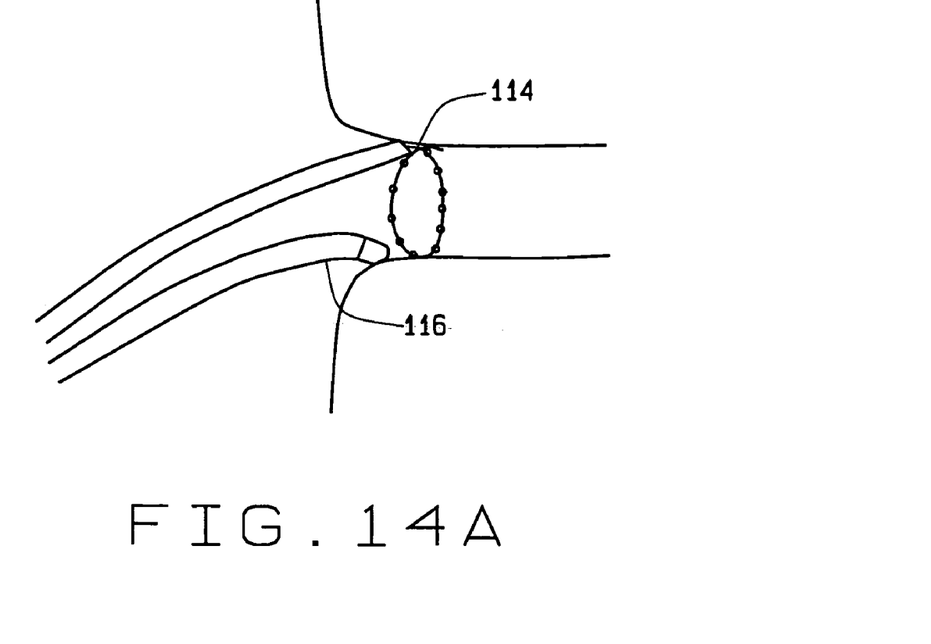
FIG. 14A shows a separate anchor member and ablation member used in performing a pulmonary vein isolation.
Figure 14B:
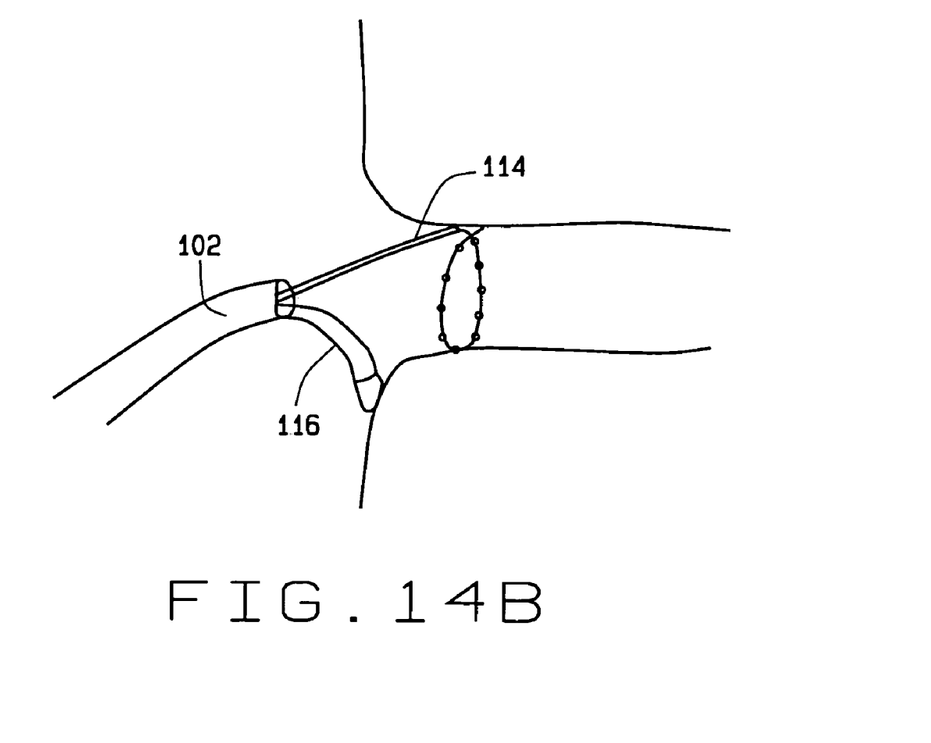
FIG. 14B shows a combined anchor member and ablation member performing a pulmonary vein isolation with a common, closely spaced pivot point.

FIGS. 14A and 14B illustrate the advantage of combining the anchor member 114 and the ablation member 116. As shown in FIG. 14A, the anchor member and ablation member 116 are essentially separate, and must be independently controlled. As shown in FIG. 14B, when incorporated as device 100, the distal end 106 of the catheter 102 provides a close pivot point, facilitating the navigation of the ablation member 116 to the various points identified by the electrodes on the anchor member. Even using magnetic navigation in accordance with the principles of this invention, the closely spaced pivot point makes performing the procedure in 14B easier than in 14A.

In any of the embodiments, localization system can be included for localization the position and/or orientation of the mapping or ablation element. For example RF localization elements, electri-potential localization elements, ultrasonic transducers, or radiopaque markers can be included in the devices so that their positions can be determined with well know localization systems. The ability to localize the devices facilitates the ability to automate at least the mapping, and potentially the ablation as well. The magnetic navigation system and an automatic device advancer controlling the position and orientation, and the localization system providing feedback of the current position and orientation.

What is claimed is:

1. A catheter for forming an ablation pattern to electrically isolate a vessel having an ostium from a chamber formed within a patient for treatment of cardiac arrhythmia, the catheter having a distal end navigable to the chamber, an anchor member telescopingly deployable from the distal end of the catheter and having a member for temporarily securing the anchor member in a vessel, and an ablation member telescopingly deployable from the distal end of the catheter, wherein the end of the catheter is held is place by the anchor member, and the portion of the ablation member extending from the distal end of the catheter is magnetically navigable and is capable of being pivotally oriented about the distal end of the catheter being held, to facilitate magnetic navigation of the ablation member to contact a point on the tissue surrounding the ostium of the vessel in which the anchor member is secured.

* * * * *